US009260387B2

(12) United States Patent
Dakka et al.

(10) Patent No.: US 9,260,387 B2
(45) Date of Patent: Feb. 16, 2016

(54) PROCESS FOR PRODUCING PHENOL

(71) Applicant: ExxonMobil Chemical Patents Inc., Baytown, TX (US)

(72) Inventors: Jihad M. Dakka, Whitehouse Station, NJ (US); Edmund J. Mozeleski, Somerset, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/441,194

(22) PCT Filed: Nov. 22, 2013

(86) PCT No.: PCT/US2013/071434
§ 371 (c)(1),
(2) Date: May 7, 2015

(87) PCT Pub. No.: WO2014/088842
PCT Pub. Date: Jun. 12, 2014

(65) Prior Publication Data
US 2015/0251997 A1    Sep. 10, 2015

Related U.S. Application Data

(60) Provisional application No. 61/735,655, filed on Dec. 11, 2012, provisional application No. 61/734,202, filed on Dec. 6, 2012, provisional application No. 61/734,213, filed on Dec. 6, 2012.

(30) Foreign Application Priority Data

Feb. 8, 2013  (EP) ..................... 13154526

(51) Int. Cl.
| | | |
|---|---|---|
| C07C 45/53 | (2006.01) | |
| C07C 37/08 | (2006.01) | |
| C07C 2/66 | (2006.01) | |
| C07C 407/00 | (2006.01) | |
| C07C 29/80 | (2006.01) | |
| C07C 37/74 | (2006.01) | |
| C07C 1/22 | (2006.01) | |
| C07C 45/82 | (2006.01) | |
| C07C 1/24 | (2006.01) | |
| C07C 5/05 | (2006.01) | |

(52) U.S. Cl.
CPC ................. *C07C 407/00* (2013.01); *C07C 1/22* (2013.01); *C07C 1/24* (2013.01); *C07C 5/05* (2013.01); *C07C 29/80* (2013.01); *C07C 37/08* (2013.01); *C07C 37/74* (2013.01); *C07C 45/53* (2013.01); *C07C 45/82* (2013.01); *C07C 2101/14* (2013.01); *C07C 2101/16* (2013.01); *C07C 2521/04* (2013.01); *C07C 2529/74* (2013.01)

(58) Field of Classification Search
CPC ............ C07C 45/53; C07C 37/08; C07C 2/66
USPC ........................................ 568/376, 798, 799
See application file for complete search history.

(56) References Cited

U.S. PATENT DOCUMENTS

| | | | |
|---|---|---|---|
| 3,049,447 A | | 8/1962 | Knapp |
| 3,959,381 A | | 5/1976 | Arkell et al. |
| 4,147,726 A | | 4/1979 | Wu |
| 4,160,000 A | | 7/1979 | Hutto et al. |
| 4,358,618 A | | 11/1982 | Sifniades et al. |
| 4,439,409 A | * | 3/1984 | Puppe et al. ................. 423/706 |
| 4,954,325 A | * | 9/1990 | Rubin et al. ................. 423/706 |
| 5,250,277 A | * | 10/1993 | Kresge et al. ............. 423/329.1 |
| 6,037,513 A | | 3/2000 | Chang et al. |
| 6,720,462 B2 | | 4/2004 | Kuhnle et al. |
| 6,852,893 B2 | | 2/2005 | Kuhnle et al. |
| 2002/0169331 A1 | | 11/2002 | Miura et al. |
| 2011/0301387 A1 | | 12/2011 | Wang et al. |

FOREIGN PATENT DOCUMENTS

| | | | |
|---|---|---|---|
| CN | | 1962574 | 5/2007 |
| CN | | 101560396 | * 10/2009 |
| EP | | 1074536 | 2/2001 |
| WO | WO 2009/025939 | | 2/2009 |
| WO | WO 2009/058527 | | 5/2009 |
| WO | WO 2009/058531 | | 5/2009 |
| WO | WO 2009/128984 | | 10/2009 |
| WO | WO 2009/131769 | | 10/2009 |
| WO | WO 2009/098916 A2 | * | 9/2010 |
| WO | WO 2010/098916 | | 9/2010 |
| WO | WO 2012/036822 | | 3/2012 |
| WO | WO 2012/036826 | | 3/2012 |
| WO | WO 2012/036827 | | 3/2012 |
| WO | WO 2014/043188 | | 3/2014 |
| WO | WO 2014/043478 | | 3/2014 |
| WO | WO 2014/081597 | | 5/2014 |
| WO | WO 2014/088841 | | 6/2014 |
| WO | WO 2014/088842 | | 6/2014 |

* cited by examiner

*Primary Examiner* — Sikarl Witherspoon
(74) *Attorney, Agent, or Firm* — Siwen Chen; Stephen A. Baehl

(57) ABSTRACT

In a process for producing phenol and/or cyclohexanone, cyclohexylbenzene is contacted with an oxygen-containing gas under conditions effective to produce an oxidation effluent containing cyclohexylbenzene hydroperoxide. At least a portion of the oxidation effluent containing cyclohexylbenzene hydroperoxide is then contacted with a cleavage catalyst under conditions effective to produce a cleavage effluent containing phenol and cyclohexanone. At least one of the oxidation effluent and the cleavage effluent contains a by-product comprising a mixture of isomers of phenylcyclohexanol and/or phenylcyclohexanone, in which the 2-phenyl isomer(s) is present in an amount less than 20% of the mixture. At least a portion of the at least one effluent containing the isomer mixture is contacted with a dehydration catalyst under conditions effective to convert at least a portion of the mixture to isomers of phenylcyclohexene, with very low ring rearrangement to produce 1-methylcyclopentenylbenzene and cyclopentenylmethylbenzene.

21 Claims, 1 Drawing Sheet

PROCESS FOR PRODUCING PHENOL

PRIORITY CLAIM TO RELATED APPLICATIONS

This application is a National Stage Application of International Application No. PCT/US2013/071434 filed Nov. 22, 2013, which claims priority to U.S. Provisional Application Ser. Nos. 61/735,655 filed Dec. 11, 2012; 61/734,202, filed Dec. 6, 2012; 61/734,213, filed Dec. 6, 2012, and European Application No. 13154526.1 filed Feb. 8, 2013; the disclosures of which are fully incorporated herein by their reference.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, a common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide in the presence of heterogeneous or homogenous catalysts into substantially equimolar amounts of phenol and acetone. However, the world demand for phenol is growing more rapidly than that for the acetone co-product.

Thus, a process that avoids or reduces the use of propylene as a feed and coproduces higher ketones, rather than acetone, may be an attractive alternative route to the production of phenol. For example, there is a growing market for cyclohexanone, which is used as an industrial solvent, as an activator in oxidation reactions and in the production of adipic acid, cyclohexanone resins, cyclohexanone oxime, caprolactam, and nylon 6.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is via benzene hydroalkylation in which benzene is contacted with hydrogen in the presence of a catalyst such that a portion of the benzene is converted into cyclohexene which then reacts with the remaining benzene to produce the desired cyclohexylbenzene. One such method is disclosed in U.S. Pat. No. 6,037,513, in which the catalyst comprises a molecular sieve of the MCM-22 type and at least one hydrogenation metal selected from palladium, ruthenium, nickel, cobalt, and mixtures thereof. This reference also discloses that the resultant cyclohexylbenzene can be oxidized to the corresponding hydroperoxide, which is then decomposed to the desired phenol and cyclohexanone co-product in roughly equimolar amounts.

Several technical challenges not seen in the cumene-based Hock process exist in producing phenol via cyclohexylbenzene. One such challenge is that non-negligible amounts of by-products, including phenylcyclohexanols and phenylcyclohexanones, are generated during the oxidation step. To improve process economics, it would be desirable to develop a process for converting these phenylcyclohexanols and phenylcyclohexanones to useful products. In seeking to develop such a process, the present inventors have found that phenylcyclohexanols and phenylcyclohexanones can be converted back to cyclohexylbenzene in high yield by a combination of dehydration and hydrogenation. However, investigation of this process has also demonstrated that, particularly with the 2-phenyl isomers, such as 2-phenyl-1-cyclohexanol and 2-phenyl-1-cyclohexanone, the dehydration step is accompanied by isomerization of the 2-phenylcyclohexene intermediate to 1-methylcyclopentenylbenzene and cyclopentenylmethylbenzene. On hydrogenation, these products are converted to 1-methylcyclopentylbenzene and cyclopentylmethylbenzene, which are difficult to remove from the hydrogenation effluent by either physical or chemical techniques.

SUMMARY

According to the present disclosure, it has now been found that, by controlling the cyclohexylbenzene oxidation step, it is possible to maintain the total amount of 2-phenyl-1-cyclohexanol and 2-phenyl-1-cyclohexanone at a level less than 20% of all phenylcyclohexanol isomers and phenylcyclohexanone isomers. One suitable mode of control is by selecting a cyclic imide as the oxidation catalyst. In this way, dehydration and hydrogenation of the phenylcyclohexanol/phenylcyclohexanone by-product leads to negligible amounts (less than 5000 ppm) of 1-methylcyclopentenylbenzene and cyclopentenylmethylbenzene, and the yield of cyclohexylbenzene in the hydrogenation step is improved.

In one aspect, a first aspect of the present disclosure relates to a process for producing phenol and/or cyclohexanone, the process comprising:

(a) contacting cyclohexylbenzene with an oxygen-containing gas under conditions effective to produce an oxidation effluent containing cyclohexylbenzene hydroperoxide;

(b) contacting at least a portion of the oxidation effluent containing cyclohexylbenzene hydroperoxide with a cleavage catalyst under conditions effective to produce a cleavage effluent containing phenol and cyclohexanone, wherein the oxidation effluent and/or the cleavage effluent contains a by-product comprising of one or more phenylcyclohexanol isomer and/or one or more phenylcyclohexanone isomer, in which the total weight of 2-phenyl-1-cyclohexanol and 2-phenyl-1-cyclohexanone is less than 20% of the total weight of all phenylcyclohexanol isomers and all phenylcyclohexanone isomers;

(c) contacting at least a portion of at least one of the oxidation effluent and the cleavage effluent containing the by-product with a dehydration catalyst under conditions effective to convert at least a portion of the one or more phenylcyclohexanol isomer and at least a portion of the one or more phenylcylcohexanone isomer to phenylcyclohexene; and optionally (d) contacting at least a portion of the phenylcyclohexene produced in the contacting step (c) with hydrogen under conditions effective to convert at least a portion of the phenylcyclohexene to a product comprising cyclohexylbenzene.

The contacting steps (c) and (d) may be conducted in the same reaction zone, in the presence of a bifunctional catalyst comprising a solid acid dehydration component, such as a molecular sieve and especially a molecular sieve of the MCM-22 type, and a hydrogenating metal component, such as at least one metal selected from Groups 6 to 12 of the Periodic Table of Elements, especially palladium.

The conditions in the contacting step (c) can comprise a temperature of 25° C. to 200° C. and the conditions in the contacting step (d) comprise a temperature of 80° C. to 150° C. and a hydrogen partial pressure of 15 kPa to 1000 kPa.

The process can further comprise:

(e) separating at least a portion of the cleavage effluent from the contacting step (b) into a first fraction containing phenol and cyclohexanone and a second fraction containing the by-product at a higher concentration than the first fraction; and (f) supplying the second fraction to the contacting step (c).

The separating step (e) can be effected in a distillation column and at least a portion of the product produced in the contacting step (d) is fed back to the distillation column.

The cleavage catalyst can comprise sulfuric acid. In such case, the process can further comprise the following steps:

(g) neutralizing residual sulfuric acid in the cleavage effluent with an amine to produce an amine salt; and (h) removing the amine salt produced by the neutralizing step (g) prior to the separating step (e).

The removing step (h) can be effected in a further distillation column.

The present disclosure also relates to a feed composition comprising cyclohexylbenzene and a mixture of at least two of 2-phenyl-1-cyclohexanol, 3-phenyl-1-cyclohexanol, and 4-phenyl-1-cyclohexanol, in which the amount of 2-phenyl-1-cyclohexanol, if present, is less than 20 wt % of the mixture.

The present disclosure also relates to a feed composition comprising cyclohexylbenzene and a mixture of at least two of 2-phenyl-1-cyclohexanone, 3-phenyl-1-cyclohexanone, and 4-phenyl-1-cyclohexanone, in which the amount of 2-phenyl-1-cyclohexanone, if present, is less than 20 wt % of the mixture.

The present disclosure further relates to a feed composition comprising cyclohexylbenzene and a mixture of at least two of 2-phenyl-1-cyclohexanone, 3-phenyl-1-cyclohexanone, 4-phenyl-1-cyclohexanone, 2-phenyl-1-cyclohexanol, 3-phenyl-1-cyclohexanol, and 4-phenyl-1-cyclohexanol, in which the total amount of 2-phenyl-1-cyclohexanone and 2-phenyl-1-cyclohexanol, if present, is less than 20 wt % of the mixture.

DETAILED DESCRIPTION OF THE EMBODIMENTS

Figure 1:
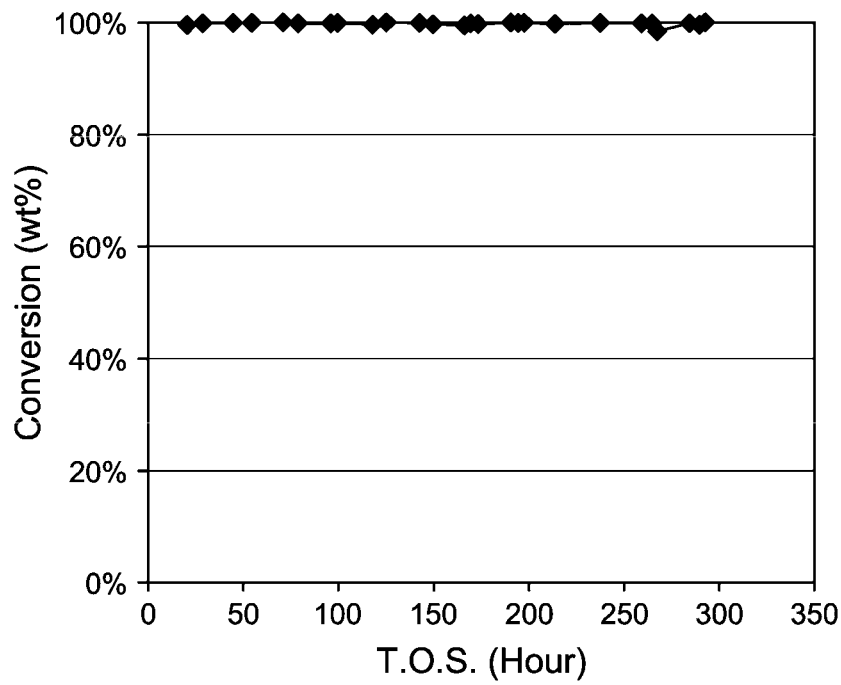
FIG. 1 is a graph of feed conversion against time on stream in hours for the process of the example.

In the present disclosure, a process may be described as comprising of at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, some steps may be conducted simultaneously, for example, in the same reaction zone. Preferably, steps are performed in the order listed.

Unless otherwise indicated, all numbers in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenating metal" include embodiments where one, two, or more hydrogenating metals are used, unless specified to the contrary or the context clearly indicates that only one hydrogenating metal is used.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzene, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene and 1,3,5-tricyclohexylbenzene, and combinations and mixtures thereof at any proportion. The generic term "polycycloyhexylbenzene" shall include any of the dicyclohexylbenzene isomers and tricyclohexylbenzene isomers described above, and combinations and mixtures of at least two thereof in any proportion.

As used herein, the term "effluent" generally means the product of a given step or operation. Thus, the effluent can be a stream of material flowing from a vessel in a continuous process or the product from a batch or semi-batch process.

A process is described herein for producing phenol and/or cyclohexanone from cyclohexylbenzene. In the process, cyclohexylbenzene is initially oxidized to produce cyclohexylbenzene hydroperoxide, which can then be cleaved to generate the desired phenol and cyclohexanone. However, the oxidation step also produces by-products, including isomers of phenylcyclohexanol and phenylcyclohexanone, which in the present process are dehydrated to phenylcyclohexene which can then be hydrogenated back to cyclohexylbenzene for recycle to the oxidation step. By controlling the oxidation reaction so that the amount of the 2-phenyl isomers in the mixture of phenylcyclohexanol and phenylcyclohexanone isomers present in the oxidation product is maintained below 20 wt % of the mixture, it is found that the dehydration step to phenylcyclohexene is accompanied by little or no ring rearrangement to 1-methylcyclopentenylbenzene and cyclopentenylmethylbenzene.

Preferably, the process of the present disclosure forms part of an integrated process for producing phenol from benzene in which the benzene is initially alkylated or hydroalkylated to produce the cyclohexylbenzene feed to the present process. The ensuing description will therefore focus on this integrated process.

Production of Cyclohexylbenzene

The cyclohexylbenzene starting material for the present process can be produced by the alkylation of benzene with cyclohexene according to the following reaction:

The cyclohexene can be supplied to the reaction zone as a separate feed from the benzene, but normally is produced in situ by the selective hydrogenation of benzene in the presence of a bifunctional catalyst. Such a reaction is generally termed "hydroalkylation" and may be summarized as follows:

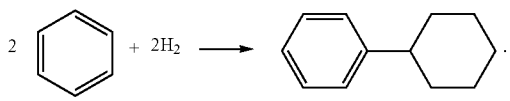

Any commercially available benzene feed can be used in the hydroalkylation step, but preferably the benzene has a purity level of at least 99 wt %. Similarly, although the source of hydrogen is not critical, it is desirable that the hydrogen is at least 99 wt % pure.

The total feed to the hydroalkylation step may contain less than 1000 ppm, such as less than 500 ppm, for example less than 100 ppm, water. In addition, the total feed may contain less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but is desirably arranged such that the molar ratio of hydrogen to benzene in the hydroalkylation feed is from about 0.15:1 to about 15:1, such as from about 0.4:1 to about 4:1, for example from about 0.4:1 to about 0.9:1.

In addition to the benzene and hydrogen, a diluent, which is substantially inert under hydroalkylation conditions, may be supplied to the hydroalkylation reaction. The diluent may be a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, advantageously the diluent is added in an amount such that the weight ratio of the diluent to the aromatic compound is at least 1:100; for example at least 1:10, but no more than 10:1, for example no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from about 100° C. to about 400° C., such as from about 125° C. to about 250° C., while suitable reaction pressures are from about 100 kPa to about 7,000 kPa, such as from about 500 kPa to about 5,000 kPa.

The catalyst employed in the hydroalkylation reaction is a bifunctional catalyst comprising a hydrogenating metal component and an alkylating solid acid component. Advantageously, the alkylating solid acid component comprises a molecular sieve of the MCM-22 type. The term "MCM-22 type material" (or "material of the MCM-22 type" or "molecular sieve of the MCM-22 type"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth Edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 type generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Preferably, the molecular sieve is selected from (a) MCM-49; (b) MCM-56; and (c) isotypes of MCM-49 and MCM-56, such as ITQ-2. Other molecular sieves, such as UZM-8 (described in U.S. Pat. No. 6,756,030) may be used alone or along with the MCM-22 type molecular sieves for the hydroalkylation reaction described herein.

Any known hydrogenating metal can be employed in the hydroalkylation catalyst, although suitable metals include palladium, ruthenium, nickel, zinc, tin, and cobalt, with palladium being particularly advantageous. Desirably, the amount of hydrogenating metal present in the catalyst is from about 0.05 wt % to about 10 wt %, such as from about 0.1 wt % to about 5.0 wt %, of the catalyst. Where the MCM-22 type molecular sieve is an aluminosilicate, the amount of hydrogenating metal present can be such that the molar ratio of the aluminum in the molecular sieve to the hydrogenating metal is from about 1.5 to about 1500, for example from about 75 to about 750, such as from about 100 to about 300.

The hydrogenating metal may be directly supported on the MCM-22 type molecular sieve by, for example, impregnation or ion exchange. Preferably, at least 50 wt %, for example at least 75 wt %, and desirably substantially all of the hydrogenating metal is supported on an inorganic oxide separate from, but composited with, the molecular sieve. In particular, it is found that by supporting the hydrogenating metal on the inorganic oxide, the activity of the catalyst and its selectivity to cyclohexylbenzene and dicyclohexylbenzene are increased as compared with an equivalent catalyst in which the hydrogenating metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenating metal is deposited on the inorganic oxide by, e.g., impregnation, before the metal-containing inorganic oxide is composited with the molecular sieve. The catalyst composite may be produced by co-pelletization, in which a mixture of the molecular sieve and the metal-containing inorganic oxide are formed into pellets at high pressure (desirably about 350 kPa to about 350,000 kPa), or by co-extrusion, in which a slurry of the molecular sieve and the metal-containing inorganic oxide, optionally together with a separate binder, are forced through a die. If necessary, additional hydrogenating metal can subsequently be deposited on the resultant catalyst composite.

Although the hydroalkylation reaction using an MCM-22 type molecular sieve catalyst is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, and mordenite. The transalkylation reaction is desirably conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio about of 1:1 to about 5:1.

Dealkylation or cracking is also desirably effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia and mixtures thereof. Desirably, the acid catalyst includes at least one aluminosilicate, aluminophosphate or silicoaluminophosphate of the FAU, AEL, AFI, and MWW type. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, hydrogen is advantageously introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least a portion of the cyclohexane in the $C_6$-rich stream portion to benzene, which again can be recycled to the hydroalkylation reaction. The dehydrogenation catalyst desirably comprises (a) a support; (b) a hydrogenation-dehydrogenation component; and (c) an inorganic promoter. The support (a) may be selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds, and mixtures thereof. Desirably, the hydrogenation-dehydrogenation component is present in an amount from about 0.1 wt % to about 10 wt % of the catalyst. A suitable inorganic promoter (c) comprises at least one metal or compound thereof selected from Group 1 of the Periodic Table of Elements, such as a potassium compound. Desirably, the promoter is present in an amount from about 0.1 wt % to about 5.0 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 $hr^{-1}$ to 50 $hr^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least a portion of the hydroalkylation reaction product may be treated with a catalyst under conditions to remove at least 1,1-methylcyclopentylbenzene and/or bicyclohexyl from the product. The catalyst can be an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

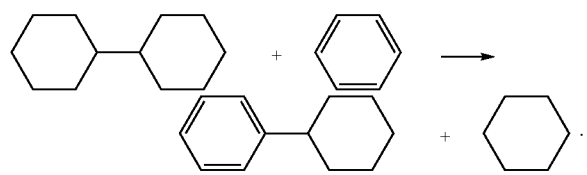

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed herein is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation step can be conducted autogeneously or more preferably in the presence of a catalyst. Although any catalyst can be employed, a preferred oxidation catalyst includes an N-hydroxy substituted cyclic imide described in U.S. Pat. No. 6,720,462, which is incorporated herein by reference in its entirety for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy (pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo [2.2.1 ]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5.0 wt %, of the cyclohexylbenzene.

Suitable conditions for the oxidation step include a temperature in a range from T1° C. to T2° C. and an absolute pressure in the reactor in the range from P1 kPa and P2 kPa, where: T1 can be 60, 65, 70, 75, 80, 85, 90, 95, or 100; T2 can be 200, 195, 190, 185, 180, 170, 165, 160, 155, 150, 145, 140, 135, or 130; P1 can be 50, 60, 70, 80, 90, 100, 110, 120, 130, 140, 150, 160, 180, 200; and P2 can be 10,000, 9,000, 8,000, 7,000, 6,000, 5,000, 4,000, 3,000, 2,000, or 1,000. A particularly advantageous temperature range is from 60° C. to 150° C., such as from 70° C. to 130° C., or from 70° C. to 120° C., or from 70° C. to 110° C., or from 70° C. to 100° C., in obtaining both a desirable reaction rate, conversion and selectivity, especially a low, desired concentration of 2-phenyl-1-cyclohexanol and 2-phenyl-1-cyclohexanone in the oxidation effluent. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. The oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. Alternatively, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Desirably, the product of the cyclohexylbenzene oxidation reaction contains at least 5.0 wt %, such as at least 10 wt %, for example at least 15 wt %, or at least 20 wt % cyclohexyl-1-phenyl-1-hydroperoxide based upon the total weight of the oxidation reaction effluent. Desirably, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

In addition to the desired cyclohexyl-1-phenyl-1-hydroperoxide (formula (F-I) below), the oxidation step tends to produce some by-products which, if not removed and/or converted to useful materials would result in loss of valuable feed and/or could adversely influence downstream processes. Among these by-products are isomers of phenylcyclohexanol and phenylcyclohexanone. Potential isomers of phenylcyclohexanol include 1-phenyl-1-cyclohexanol (formula (F-II) below), 2-phenyl-1-cyclohexanol (formula (F-III) below), 3-phenyl-1-cyclohexanol (formula (F-IV) below) and 4-phenyl-1-cyclohexanol (formula (F-V) below). As used herein, the generic term "phenylcyclohexanol," when used either in the singular or plural form, shall include all isomers thereof disclosed above and any mixtures comprising two or more of the isomers, unless specified or indicated to mean only one specific isomer. Potential isomers of phenylcyclohexanone include 2-phenyl-1-cyclohexanone (formula (F-VI) below), 3-phenyl-1-cyclohexanone (formula (F-VII) below) and 4-phenyl-1-cyclohexanone (formula (F-VIII) below). As used herein, the generic term "phenylcyclohexanone," when used either in the singular or plural form, shall include all isomers disclosed above and any mixtures thereof comprising two or more of the isomers, unless specified or otherwise indicated to mean only one specific isomer. As used herein, the term "2-phenyl isomers" include both 2-phenyl-1-cyclohexanol and 2-phenyl-1-cyclohexanone.

(F-I)

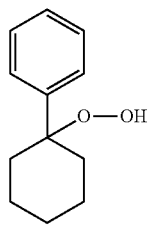

(F-II)

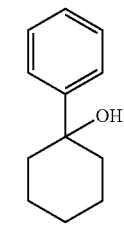

(F-III)

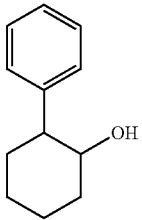

(F-IV)

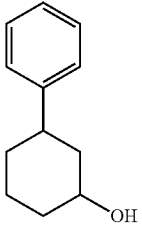

(F-V)

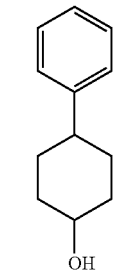

(F-VI)

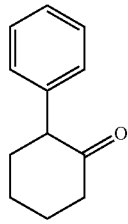

(F-VII)

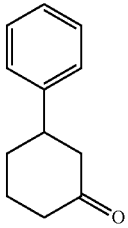

(F-VIII)

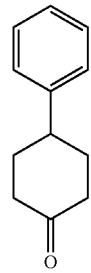

However, by controlling the oxidation reaction conditions, such as temperature, pressure, and particularly, by effecting the oxidation in the presence of a cyclic imide catalyst such as NHPI, it is found that the level of 2-phenyl-1-cyclohexanol can be less than 20%, such as less than 10%, for example less than 5.0%, even less than 1.0%, of the total amount of phenylcyclohexanol in the oxidation effluent. Similarly, the level of 2-phenyl-1-cyclohexanone can be less than 20%, such as less than 10%, for example less than 5.0%, even less than 1.0%, of the total amount of phenylcyclohexanone in the oxidation effluent. Also, for example, the total of the 2-phenyl isomers can be less than 20 wt %, such as less than 10 wt %, for example less than 5.0 wt %, even less than 1.0 wt % of the total amount of the phenylcyclohexanol and phenylcyclohexanone isomers in the oxidation effluent.

Desirably, the phenylcyclohexanols are present in the oxidation reaction effluent in an amount from 0.1 wt % to 10 wt % of the effluent and the phenylcyclohexanones are present in an amount from 0.1 wt % to 5.0 wt % of the effluent. In the present process, these by-products are removed and desirably converted to useful cyclohexylbenzene, which can then be recycled to the oxidation step. However, as explained below, removal and conversion of these by-products is desirably conducted after the downstream cleavage step.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step. Other hydroperoxides that may be present in the oxidation effluent stream may also undergo acid-catalyzed cleavage along with the desired cyclohexyl-1-phenyl-1-hydroperoxide.

Desirably, the acid catalyst used in the cleavage reaction is at least partially soluble in the cleavage effluent, is stable at a temperature of at least 185° C. and has a lower volatility (higher normal boiling point) than cyclohexylbenzene. Desirably, the acid catalyst is also at least partially soluble in the cleavage reaction product. Suitable homogeneous acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

The cleavage effluent may contain at least 50 weight-parts-per-million (wppm) and no greater than 5000 wppm of the acid catalyst, or at least 100 wppm and no greater than 3000 wppm, or at least 150 wppm and no greater than 2000 wppm of the acid catalyst, or at least 300 wppm and no greater than 1500 wppm of the acid catalyst, based upon total weight of the cleavage effluent.

A heterogeneous acid catalyst may be employed for the cleavage reaction, such as molecular sieve, and in particular a molecular sieve having a pore size in excess of 6.1 Å. Examples of suitable molecular sieves include zeolite beta, zeolite Y, zeolite X, ZSM-12, and mordenite. The molecular sieve may comprise a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Advantageously, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

The cleavage reaction mixture may include cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Advantageously, the cleavage reaction is conducted under conditions including a temperature in a range from T3° C. to T4° C. and an absolute pressure in the reactor in a range from P3 kPa to P4 kPa, where: T3 can be 20, 25, 30, 35, 40, 45, 50, 55, or 60; T4 can be 200, 190, 180, 170, 160, 150, 140, 130, 120, 100, 90, or 80; P3 can be 50, 60, 80, 100, 150, 200, 250, 300, 350, 400, 450, or 500; and P4 can be 1000, 900, 800, 700, 600, 500, or 400, to the extent P3<P4. It is highly desired that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. Alternatively, the cleavage reactor comprises a plurality of reactors in series, each performing a portion of the conversion reaction, optionally operating in different modes and at different conditions selected to enhance the cleavage reaction at the pertinent conversion range. The cleavage reactor can be a catalytic distillation unit.

The cleavage reactor can be operated to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can be used to remove at least a part of the heat generated.

The major product of the cleavage reaction is desirably a substantially equimolar mixture of phenol and cyclohexanone.

Treatment of Phenylcyclohexanol and Phenylcyclohexanone By-Products

As indicated above the oxidation step produces non-insignificant quantity of phenylcyclohexanol and/or phenylcyclohexanone by-products which, in the present process, are converted back to cyclohexylbenzene. Although the conversion can be conducted directly after the oxidation step, it is more advantageously conducted after the cleavage reaction. The effluent from cleavage reaction may contain residual sulfuric acid cleavage catalyst in addition to the phenol and cyclohexanone products and the phenylcyclohexanol and/or phenylcyclohexanone by-products. In this case, the residual sulfuric acid in the cleavage reaction effluent may be first neutralized by treating the cleavage effluent with one or more amines or diamines to produce amine salts. The amine salts are then removed from the neutralized cleavage effluent, desirably by an initial distillation step, with the amine salts being removed as part of the heavies. The remainder of the neutralized cleavage effluent can then be further separated, advantageously by a further distillation step, into a light fraction containing phenol and cyclohexanone and a heavy fraction containing the phenylcyclohexanol and/or phenylcyclohexanone by-products. The heavy fraction is then fed to a dehydration reaction zone, advantageously a fixed bed reactor, for conversion of the phenylcyclohexanol and/or phenylcyclohexanone to phenylcyclohexenes, which include 2-phenyl-1-cyclohexene (formula (F-IX) below), 3-phenyl-1-cyclohexene (formula (F-X) below) and 4-phenyl-1-cyclohexene (formula (F-XI) below). As used herein, the generic term "phenylcyclohexene," when used either in singular or plural form, includes all the isomers disclosed above and any mixtures of two or more thereof, unless specified or otherwise indicated to mean only one specific isomer.

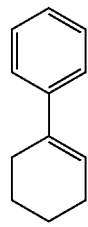

(F-IX)

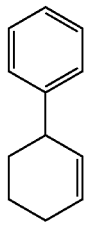

(F-X)

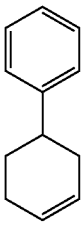

(F-XI)

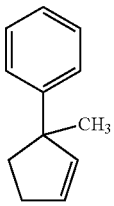

(F-XII)

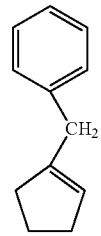

(F-XIII)

Dehydration of the phenylcyclohexanols to phenylcyclohexene can be effected over a solid acid catalyst such as zeolite Y, zeolite beta or, more preferably, a member of the MCM-22 type comprising a molecular sieve of the MCM-22 type. Preferably, the molecular sieve of the MCM-22 type is MCM-49 or MCM-56. The catalyst may also contain an inorganic oxide binder, such as silica, alumina, or silica/alumina For example, the dehydration reaction is advantageously conducted at a temperature of 25° C. to 200° C., such as 80° C. to 150° C., a pressure of 15 kPa to 500 kPa and a weight hourly space velocity of 0.1 $hr^{-1}$ to 50 $hr^{-1}$. As a result of the low level of 2-phenyl isomers in the feed, the product of dehydration reaction is found to contain very low amounts, desirably less than 5000 ppm by weight, such as less than 1000 ppm by weight, for example less than 100 ppm by weight, even less than 10 ppm by weight, of 1-methylcyclopentenylbenzene (formula (F-XII) above) and cyclopentenylmethylbenzene (formula (F-XIII) above) in total. The 1-methylcyclopentenylbenzene (formula (F-XII) above) and cyclopentenylmethylbenzene (formula (F-XIII) above) by-products, if present, are very reactive and may undergo reactions such as dimerization, alkylation, and polymerization, all of which would result in the formation of heavy products, leading to loss of overall yield of phenol and/or cyclohexanone, and complicate downstream separation and other operations.

The phenylcyclohexene-product of the dehydration reaction is then contacted with hydrogen in a hydrogenation reaction zone, which is advantageously operated at a temperature of 80° C. to 150° C., such as 80° C. to 120° C., and a hydrogen partial pressure of 15 kPa to 1000 kPa, such as 15 kPa to 300 kPa. The hydrogenation is desirably conducted in the presence of a catalyst comprising of at least one metal selected from Groups 6 to 12 of the Periodic Table of Elements, preferably palladium, on an inorganic support, such as silica. The phenylcyclohexenes (formula (F-IX), (F-X) and (F-XI) above) are thereby converted to cyclohexylbenzene, which can then be recycled to the oxidation stage to enhance the yield of phenol and cyclohexanone. On the other hand, 1-methylcyclopentenylbenzene (formula (F-XII) above) and cyclopentenylmethylbenzene (formula (F-XIII) above), if present in the feed in the hydrogenation zone, will be converted into 1-methylcyclopentylbenzene and cyclopentylmethylbenzene, respectively, causing loss of overall cyclohexylbenzene yield in the process.

The dehydration and hydrogenation reactions can be conducted sequentially in separate reactors or in stacked beds in the same reactor. Alternatively, the dehydration and hydrogenation reactions can be conducted in the same reaction zone by employing a bifunctional catalyst comprising the solid acid component and the hydrogenating metal component described above.

It may be desirable to take a vapor or liquid side draw from either the distillation column used to remove the amine salts or from the distillation column used to separate the phenylcyclohexanol and/or phenylcyclohexanone by-products and employ this side draw as a feed to the dehydration/hydrogenation reactor. This would also allow integration of the distillation columns with the dehydration/hydrogenation reactor such that the effluent from the reactor could be fed back into the distillation column(s) to remove impurities produced in the dehydration/hydrogenation reaction.

The invention will now be more particularly described with reference to the following non-limiting example.

EXAMPLE

Into a clean dry ⅜" (9.52 mm) internal diameter stainless steel tubular reactor was charged 0.5 grams of a Pd/MCM-49/$Al_2O_3$ catalyst comprising 0.3 wt % Pd and 20 wt % $Al_2O_3$ diluted with 4.5 ml of 20/40 mesh quartz. The ⅜" (9.52 mm) tube was filled with additional 20/40 mesh quartz. The catalyst bed was placed within the heated zone of a fixed bed reactor. The temperature of the heated zone was raised to 100° C. and with the tubular reactor being maintained at atmospheric pressure, hydrogen was passed through the tubular reactor at a flow rate of 170 cc/min, together with the following feeds, each at a WHSV of 10 $hr^{-1}$:

For the first 142 hours on stream (201 in FIG. 2):
Dodecane Solvent: 95.9 wt %
Internal Standard (pentadecane): 2.5 wt %
2-phenyl-1-cyclohexanol: 0.9 wt %
4-phenyl-1-cyclohexanol: 0.1 wt %
1-phenyl-1-cyclohexene: 0.3 wt %
4-phenyl-1-cyclohexene: 0.3 wt %
For 142 to 169 hours on stream (203 in FIG. 2):
2-phenyl-1-cyclohexanol: 1.6 wt %
Internal Standard (pentadecane): 4.6 wt %
Dodecane Solvent: 93.8 wt %
For 169 to 194 hours on stream (205 in FIG. 2):
1-phenyl-1-cyclohexene: 1.93 wt %
Internal Standard (pentadecane): 15 wt %
Dodecane Solvent: 83.7 wt %

For 194 to 237 hours on stream (207 in FIG. 2):
4-phenyl-1-cyclohexene: 1.6 wt %
Internal Standard (pentadecane): 4.4 wt %
Dodecane Solvent: 94 wt %
For 237 to 267 hours on stream (209 in FIG. 2):
4-phenyl-1-cyclohexanol: 0.8 wt %
Internal Standard (pentadecane): 13.5 wt %
Dodecane Solvent: 85.7 wt %
For 267 to 292 hours on stream (211 in FIG. 2):
1-phenyl-1-cyclohexanol: 0.9 wt %
Internal Standard (pentadecane): 12.7 wt %
Dodecane Solvent: 86.4 wt %

Figure 2:
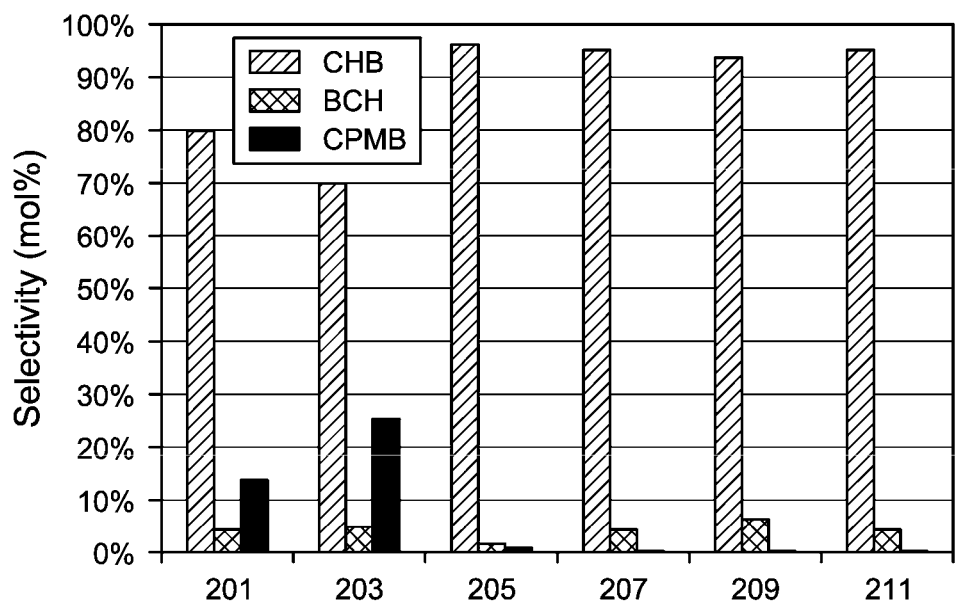
FIG. 2 is a graph showing the product selectivity for the various feeds used in the process of the example.

The results are shown in FIGS. 1 and 2, in which CHB represents cyclohexylbenzene, BCH represents bicyclohexane and CPMB represents cyclopentenylmethylbenzene. FIG. 1 shows the conversion of the alcohols over time. FIG. 2 shows the selectivities of the respective products for various feed materials. Surprisingly, as shown in FIG. 2, ring rearrangement products, such as cyclopentenylmethylbenzene (CPMB), are only produced in measurable quantities when 2-phenyl cyclohexanol is present in the feed.

While the present disclosure has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references herein are incorporated by reference in their entirety.

Non-limiting embodiments of the processes of the present disclosure include:

E1. A process for producing phenol and/or cyclohexanone, the process comprising:

(a) contacting cyclohexylbenzene with an oxygen-containing gas under conditions effective to produce an oxidation effluent containing cyclohexylbenzene hydroperoxide;

(b) contacting at least a portion of the oxidation effluent containing cyclohexylbenzene hydroperoxide with a cleavage catalyst under conditions effective to produce a cleavage effluent containing phenol and cyclohexanone, wherein the oxidation effluent and/or the cleavage effluent contains a by-product comprising of one or more phenylcyclohexanol isomer and/or one or more phenylcyclohexanone isomer, in which the total weight of 2-phenyl-1-cyclohexanol and 2-phenyl-1-cyclohexanone is less than 20% of the total weight of all phenylcyclohexanol isomers and all phenylcyclohexanone isomers;

(c) contacting at least a portion of at least one of the oxidation effluent and the cleavage effluent containing the by-product with a dehydration catalyst under conditions effective to convert at least a portion of the one or more phenylcyclohexanol isomer and at least a portion of the one or more phenylcylcohexanone isomer to phenylcyclohexene; and optionally (d) contacting at least a portion of the phenylcyclohexene produced in the contacting step (c) with hydrogen under conditions effective to convert at least a portion of the phenylcyclohexene to a product comprising cyclohexylbenzene.

E2. The process of E1, wherein step (d) is carried out.

E3. The process of E2, wherein the product of the contacting step (d) comprises less than 5000 ppm of 1-methylcyclopentenylbenzene and cyclopentenylmethylbenzene in total.

E4. The process of E2 or E3, wherein the contacting steps (c) and (d) are conducted in the same reaction zone.

E5. The process of E4, wherein the contacting steps (c) and (d) are conducted in the presence of a bifunctional catalyst comprising a solid acid dehydration component and a hydrogenating metal component.

E6. The process of E5, wherein the solid acid dehydration component comprises a molecular sieve.

E7. The process of E5 or E6, wherein the solid acid dehydration component comprises a molecular sieve of the MCM-22 type.

E8. The process of any one of E5 to E7, wherein the hydrogenating metal component comprises at least one metal selected from Groups 6 to 12 of the Periodic Table of Elements.

E9. The process of any one of E5 to E8, wherein the hydrogenating metal component comprises palladium.

E10. The process of any one of E5 to E9, wherein the bifunctional catalyst comprises from 0.1 wt % to 1.0 wt % of the hydrogenating metal component.

E11. The process of any one of E1 to E10, wherein the conditions in the contacting step (c) comprise a temperature in a range from 25° C. to 200° C.

E12. The process of any one of E1 to E11, wherein the conditions in the contacting step (d) comprise a temperature in a range from 80° C. to 150 ° C. and a hydrogen partial pressure in a range from 15 kPa to 1000 kPa.

E13. The process of any one of E1 to E12, further comprising:

(e) separating at least a portion of the cleavage effluent from the contacting step (b) into a first fraction containing phenol and cyclohexanone and a second fraction containing the by-product at a higher concentration than the first fraction; and (f) supplying the second fraction to the contacting step (c).

E14. The process of E13, wherein the separating step (e) is effected in a first distillation column.

E15. The process of E14, wherein the second fraction is removed as a side stream from the first distillation column.

E16. The process of E14 or E15, wherein step (d) is carried out, and at least a portion of the product produced in the contacting step (d) is fed back to the first distillation column.

E17. The process of any one of E13 to E16, wherein the cleavage catalyst in step (b) comprises sulfuric acid and the process further comprises:

(g) neutralizing residual sulfuric acid in the cleavage effluent with an amine to produce an amine salt; and (h) removing the amine salt prior to the separating step (e).

E18. The process of E17, wherein the removing step (h) is effected in a second distillation column.

E19. The process of any one E2 to E18, further comprising:

(i) supplying at least a portion of the cyclohexylbenzene produced in the contacting step (d) to the contacting step (a).

E20. The process of any one of E1 to E19, wherein the contacting step (a) is effected in the presence of a catalyst.

E21. The process of any one of E1 to E20, wherein the contacting step (a) is effected in the presence of a cyclic imide catalyst and at a temperature in a range from 60° C. to 200° C.

E22. The process of any one of E1 to E21, wherein the cyclohexylbenzene is produced by alkylation of benzene with cyclohexene.

E23. The process of any one of E1 to E22, wherein the cyclohexylbenzene is produced by reaction of benzene with hydrogen in the presence of a hydroalkylation catalyst.

E24. The process of E23, wherein the hydroalkylation catalyst comprises solid acid alkylation component and a hydrogenating metal component.

E25. The process of E24, wherein the solid acid alkylation component comprises a molecular sieve.

E26. The process of E24 or E25, wherein the solid acid alkylation component comprises a molecular sieve of the MCM-22 type.

E27. A feed composition comprising cyclohexylbenzene and a mixture of at least two of 2-phenyl-1-cyclohexanol, 3-phenyl-1-cyclohexanol and 4-phenyl-1-cyclohexanol, in which the amount of 2-phenyl-1-cyclohexanol, if present, is less than 20 wt % of the mixture. E28. The feed composition of E27, in which the amount of 2-phenyl-1-cyclohexanol, if present, is less than 10 wt % of the mixture.

E29. The feed composition of E27, in which the amount of 2-phenyl-1-cyclohexanol, if present, is less than 5.0 wt % of the mixture.

E30. A feed composition comprising cyclohexylbenzene and a mixture of at least two of 2-phenyl-1-cyclohexanone, 3-phenyl-1-cyclohexanone, and 4-phenyl-1-cyclohexanone, in which the amount of 2-phenyl-1-cyclohexanone, if present, is less than 20 wt % of the mixture.

E31. The feed composition of E30, in which the amount of 2-phenyl-1-cyclohexanone, if present, is less than 10 wt % of the mixture.

E32. The feed composition of E30, in which the amount of 2-phenyl-1-cyclohexanone, if present, is less than 5.0 wt % of the mixture.

E33. A feed composition comprising cyclohexylbenzene and a mixture of at least two of 2-phenyl-1-cyclohexanone, 3-phenyl-1-cyclohexanone, 4-phenyl-1-cyclohexanone, 2-phenyl-1-cyclohexanol, 3-phenyl-1-cyclohexanol, and 4-phenyl-1-cyclohexanol, in which the total amount of 2-phenyl-1-cyclohexanone and 2-phenyl-1-cyclohexanol, if present, is less than 20 wt % of the mixture.

E34. A feed composition of E33, in which the total amount of 2-phenyl-1-cyclohexanone and 2-phenyl-1-cyclohexanol, if present, is less than 10 wt % of the mixture.

E35. A feed composition of E33, in which the total amount of 2-phenyl-1-cyclohexanone and 2-phenyl-1-cyclohexanol, if present, is less than 5.0 wt % of the mixture.

The invention claimed is:

1. A process for producing phenol and/or cyclohexanone, the process comprising:
   (a) contacting cyclohexylbenzene with an oxygen-containing gas under conditions effective to produce an oxidation effluent containing cyclohexylbenzene hydroperoxide;
   (b) contacting at least a portion of the oxidation effluent containing cyclohexylbenzene hydroperoxide with a cleavage catalyst under conditions effective to produce a cleavage effluent containing phenol and cyclohexanone, wherein the oxidation effluent and/or the cleavage effluent contains a by-product comprising one or more phenyl-cyclohexanol isomer and/or one or more phenylcyclohexanone isomer, in which the total weight of 2-phenyl-1-cyclohexanol and 2-phenyl-1-cyclohexanone is less than 20% of the total weight of all phenylcyclohexanol isomers and all phenylcyclohexanone isomers;
   (c) contacting at least a portion of at least one of the oxidation effluent and the cleavage effluent containing the by-product with a dehydration catalyst under conditions effective to convert at least a portion of the one or more phenylcyclohexanol isomer and at least a portion of the one or more phenylcylcohexanone isomer to phenylcyclohexene, wherein the product of the contacting step (c) comprises less than 5000 ppm of 1-methylcyclopentenylbenzene and cyclopentenylmethylbenzene.

2. The process of claim 1, further comprising:
   (d) contacting at least a portion of the phenylcyclohexene produced in the contacting step (c) with hydrogen under conditions effective to convert at least a portion of the phenylcyclohexene to a product comprising cyclohexylbenzene.

3. The process of claim 2, wherein steps (c) and (d) are conducted in one reaction zone.

4. The process of claim 3, wherein the contacting steps (c) and (d) are conducted in the presence of a bifunctional catalyst comprising a solid acid dehydration component and a hydrogenating metal component.

5. The process of claim 4, wherein the solid acid dehydration component comprises a molecular sieve of the MCM-22 type.

6. The process of claim 4, wherein the hydrogenating metal component comprises of at least one metal selected from Groups 6 to 12 of the Periodic Table of Elements.

7. The process of claim 4, wherein the hydrogenating metal component comprises palladium.

8. The process of claim 4, wherein the bifunctional catalyst comprises from 0.1 wt % to 1.0 wt % of the hydrogenating metal component based on the total weight of the catalyst.

9. The process of claim 2, wherein the conditions in the contacting step (c) comprise a temperature in the range of from 25° C. to 200° C.

10. The process of claim 4, wherein the conditions in the contacting step (d) comprise a temperature in the range from 80° C. to 150° C. and a hydrogen partial pressure in the range from 15 kPa to 1000 kPa.

11. The process of claim 2, further comprising:
    (e) separating at least a portion of the cleavage effluent from the contacting step (b) into a first fraction containing phenol and cyclohexanone and a second fraction containing the by-product at a higher concentration than the first fraction; and
    (f) supplying the second fraction to the contacting step (c).

12. The process of claim 11, wherein the separating step (e) is effected in a first distillation column.

13. The process of claim 12, wherein the second fraction is removed as a side stream from the first distillation column.

14. The process of claim 12, wherein at least a portion of the product produced in the contacting step (d) is fed back to the first distillation column.

15. The process of claim 11, wherein the cleavage catalyst in step (b) comprises sulfuric acid and the process further comprises:
    (g) neutralizing residual sulfuric acid in the cleavage effluent with an amine to produce an amine salt; and
    (h) removing the amine salt prior to the separating step (e).

16. The process of claim 15, wherein the removing step (h) is effected in a second distillation column.

17. The process of claim 2, further comprising:
    (i) supplying at least a portion of the cyclohexylbenzene produced in the contacting step (d) to the contacting step (a).

18. The process of claim 1, wherein the contacting step (a) is effected in the presence of a cyclic imide catalyst, and at a temperature in a range from 60° C. to 200° C.

19. The process of claim 1, wherein the cyclohexylbenzene is produced by alkylation of benzene with cyclohexene.

20. The process of claim 1, wherein the cyclohexylbenzene is produced by reaction of benzene with hydrogen in the presence of a hydroalkylation catalyst.

21. The process of claim 20, wherein the hydroalkylation catalyst comprises solid acid alkylation component and a hydrogenating metal component.

* * * * *